(12) United States Patent
Rachev et al.

(10) Patent No.: US 9,135,274 B2
(45) Date of Patent: Sep. 15, 2015

(54) MEDICAL IMAGING WORKFLOW MANAGER WITH PRIORITIZED DICOM DATA RETRIEVAL

(71) Applicant: General Electric Company, Schenectady, NY (US)

(72) Inventors: Ivan Rachev, Park Ridge, NJ (US); Christopher John Olivier, Park Ridge, NJ (US); Irina Yemets, Park Ridge, NJ (US); Kirill Fakhroutdinov, Park Ridge, NJ (US)

(73) Assignee: General Electric Company, Schenectady, NY (US)

( * ) Notice: Subject to any disclaimer, the term of this patent is extended or adjusted under 35 U.S.C. 154(b) by 285 days.

(21) Appl. No.: 13/683,203

(22) Filed: Nov. 21, 2012

(65) Prior Publication Data
US 2014/0140637 A1 May 22, 2014

(51) Int. Cl.
| G06K 9/54 | (2006.01) |
| G06K 9/60 | (2006.01) |
| G06F 17/30 | (2006.01) |
| G06F 19/00 | (2011.01) |

(52) U.S. Cl.
CPC ........ *G06F 17/30268* (2013.01); *G06F 19/321* (2013.01); *G06F 19/3418* (2013.01)

(58) Field of Classification Search
CPC .............................................. G06F 17/30268
USPC ...................................................... 382/305
See application file for complete search history.

(56) References Cited

U.S. PATENT DOCUMENTS

| | | | |
|---|---|---|---|
| 6,026,365 A * | 2/2000 | Hayashi | 705/7.26 |
| 6,604,104 B1 | 8/2003 | Smith | |
| 7,702,614 B1 * | 4/2010 | Shah et al. | 707/741 |
| 7,702,618 B1 * | 4/2010 | Patterson | 707/999.003 |
| 8,090,222 B1 * | 1/2012 | Baluja et al. | 382/305 |
| 8,166,021 B1 * | 4/2012 | Cao et al. | 707/713 |
| 8,291,317 B2 * | 10/2012 | Yamamoto | 715/277 |
| 8,923,655 B1 * | 12/2014 | Weston et al. | 382/305 |
| 8,965,145 B2 * | 2/2015 | Moraleda et al. | 382/305 |
| 2001/0034786 A1 * | 10/2001 | Baumeister et al. | 709/231 |
| 2002/0152318 A1 * | 10/2002 | Menon et al. | 709/231 |
| 2002/0156973 A1 * | 10/2002 | Ulrich et al. | 711/114 |
| 2003/0005464 A1 | 1/2003 | Gropper et al. | |
| 2003/0061305 A1 * | 3/2003 | Copley et al. | 709/217 |
| 2004/0030696 A1 * | 2/2004 | Lechner | 707/7 |
| 2005/0005019 A1 * | 1/2005 | Harville et al. | 709/231 |
| 2009/0080800 A1 * | 3/2009 | Moraleda et al. | 382/276 |
| 2009/0112800 A1 * | 4/2009 | Athsani | 707/3 |
| 2009/0144781 A1 * | 6/2009 | Glaser et al. | 725/89 |
| 2009/0234965 A1 * | 9/2009 | Viveganandhan et al. | 709/231 |
| 2009/0287692 A1 * | 11/2009 | Ookuma | 707/5 |
| 2011/0060437 A1 * | 3/2011 | Durham et al. | 700/97 |

(Continued)

*Primary Examiner* — Michelle Entezari
(74) *Attorney, Agent, or Firm* — Hanley, Flight and Zimmerman, LLC

(57) ABSTRACT

Example systems and methods for retrieval and display of image data are disclosed. An example image retrieval system includes a workflow manager and an image streaming engine. The example workflow manager is to receive an image request and identify a storage location for the requested image based at least in part on metadata information. The example image streaming engine is to be associated with the storage location to stream the requested image from the storage location to a viewer, the workflow manager to select the storage location based on a location priority and to trigger streaming of the requested image from the storage location to the viewer.

10 Claims, 6 Drawing Sheets

(56) References Cited

U.S. PATENT DOCUMENTS

| | | | |
|---|---|---|---|
| 2011/0106798 A1* | 5/2011 | Li et al. | 707/728 |
| 2012/0070045 A1 | 3/2012 | Vesper et al. | |
| 2012/0166403 A1* | 6/2012 | Kim et al. | 707/692 |
| 2012/0259981 A1* | 10/2012 | Lewinski et al. | 709/225 |
| 2013/0117413 A1* | 5/2013 | Kaneko et al. | 709/217 |
| 2013/0173606 A1* | 7/2013 | Pasumarthi et al. | 707/723 |
| 2013/0318094 A1* | 11/2013 | Agro et al. | 707/741 |
| 2014/0129942 A1* | 5/2014 | Rathod | 715/720 |

* cited by examiner

MEDICAL IMAGING WORKFLOW MANAGER WITH PRIORITIZED DICOM DATA RETRIEVAL

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

Prior to the rapid onset of digital imaging, patient images were "printed" to film. The film was "hung" and viewed by radiologists, who would then dictate a report. Reports were transcribed by individuals ranging for administrative staff to medical transcriptionists and sent to ordering physician via mail or fax. Critical results were delivered by phone or pager and business statistics were managed via paper reports and spreadsheets.

As information systems for radiology came to market, the first commercially available solutions addressed the needs of the radiologist and the radiology department. These included Radiology Information Systems (RIS) and dictation transcription systems. RIS systems managed the ordering, scheduling, patient and management reporting processes while radiologists were still reading from film.

As modalities started to support the digital display of images on workstations connected to the acquisition device, Picture Archiving and Communications Systems (PACS) came to market. These centrally store images and provide radiologists with the tools to read studies on networked computer monitors, replacing both film and modality workstations.

Over time, the needs of the market have evolved from supporting specialized radiologist workflows to supporting the open and dynamic needs of the enterprise and the community. The vendor community has added systems to manage the need for advanced technologies for better diagnosis; the sharing of images between providers and organizations; to support collaboration between radiologists, physicians and teams providing care for the patient; to close the loop on reporting of critical results and manage the growing storage requirements. Often these are disparate, best-of breed systems that may or may not interoperate, increasing cost and decreasing productivity.

For example, hospitals maintain varied remote image storages that are provided by different vendors. In order to make these images available for diagnosis, diagnostic tools either pre-fetch images from these remote storages to a local storage or migrate them to another storage from which images are faster to retrieve. These operations take substantial time and precede the diagnosing of images, and, therefore they show down doctors in diagnosing and treating their patients.

BRIEF SUMMARY

Certain examples provide systems and methods for retrieval and display of image data.

Certain examples provide an image retrieval system including a workflow manager and an image streaming engine. The example workflow manager is to receive an image request and identify a storage location for the requested image based at least in part on metadata information. The example image streaming engine is to be associated with the storage location to stream the requested image from the storage location to a viewer, the workflow manager to select the storage location based on a location priority and to trigger streaming of the requested image from the storage location to the viewer.

Certain examples provide a tangible computer-readable storage medium including computer program code to be executed by a processor. The example computer program code, when executed, is to implement an image retrieval system. The example image retrieval system includes a workflow manager and an image streaming engine. The example workflow manager is to receive an image request and identify a storage location for the requested image based at least in part on metadata information. The example image streaming engine is to be associated with the storage location to stream the requested image from the storage location to a viewer, the workflow manager to select the storage location based on a location priority and to trigger streaming of the requested image from the storage location to the viewer.

Certain examples provide a method including receiving, at a workflow manager, a request for an image. The example method includes identifying, via the workflow manager, a storage location for the requested image based at least in part on associated metadata information. The example method includes selecting, via the workflow manager based on a location priority, an image streaming engine associated with the storage location to stream the requested image from the storage location to a viewer. The example method includes triggering, via the workflow manager, streaming of the requested image from the storage location to the viewer.

Figure 1:
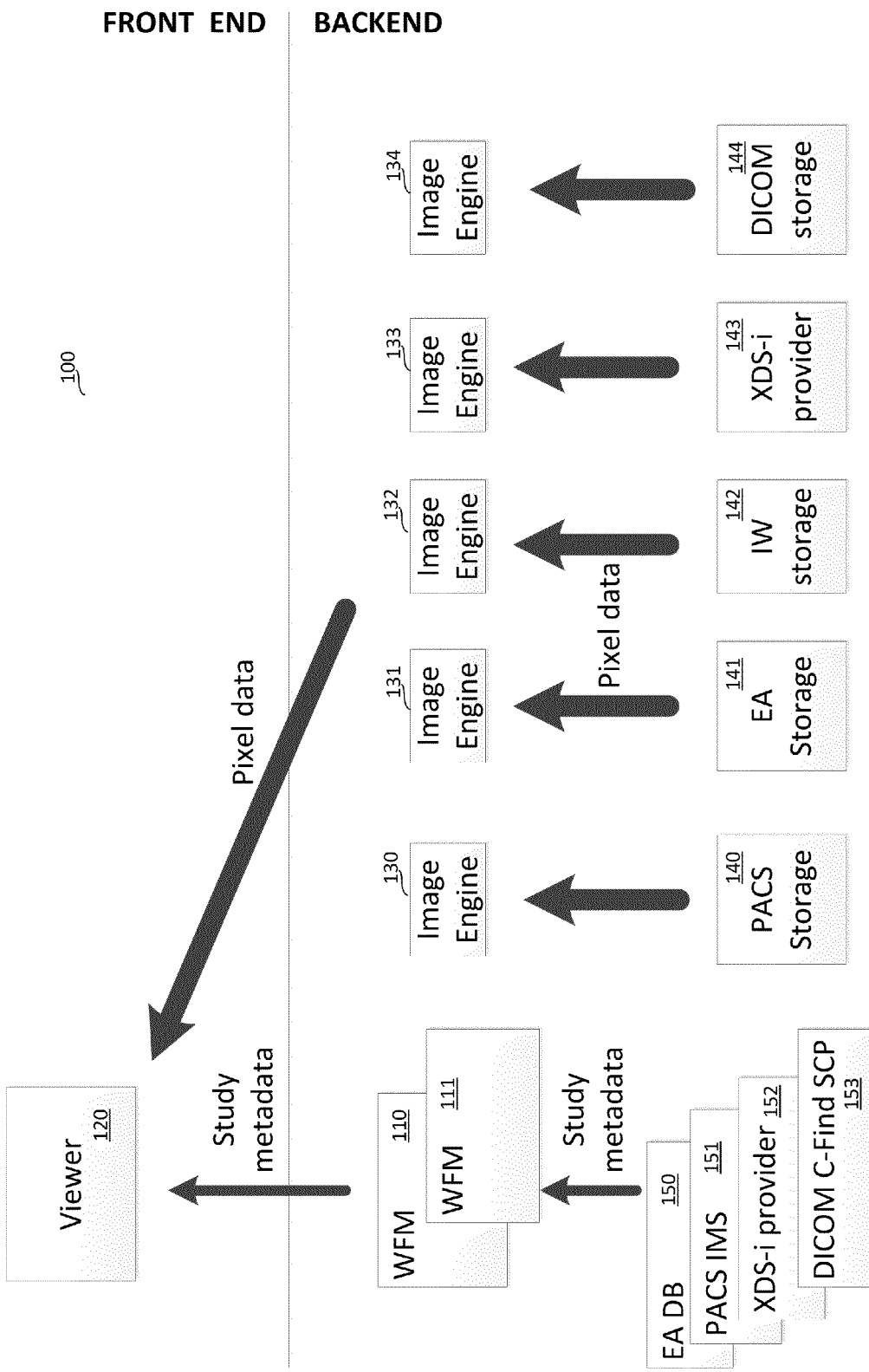
FIG. 1 illustrates an example image streaming and workflow management system.

The foregoing summary, as well as the following detailed description of certain examples of the present invention, will be better understood when read in conjunction with the appended drawings. For the purpose of illustrating the invention, certain examples are shown in the drawings. It should be understood, however, that the present invention is not limited to the arrangements and instrumentality shown in the attached drawings.

DETAILED DESCRIPTION OF CERTAIN EMBODIMENTS

In certain examples, a unified viewer workspace for radiologists and clinicians brings together capabilities with innovative differentiators that drive optimal performance through connected, intelligent workflows. The unified viewer workspace enables radiologist performance and efficiency, improved communication between the radiologist and other clinicians, and image sharing between and across organizations, reducing cost and improving care.

The unified imaging viewer displays medical images, including mammograms and other x-ray, computed tomography (CT), magnetic resonance (MR), ultrasound, and/or other images, and non-image data from various sources in a common workspace. Additionally, the viewer can be used to create, update annotations, process and create imaging models, communicate, within a system and/or across computer networks at distributed locations.

In certain examples, the unified viewer implements smart hanging protocols, intelligent fetching of patient data from within and outside a picture archiving and communication system (PACS) and/or other vendor neutral archive (VNA). In certain examples, the unified viewer supports image exchange functions and implements high performing streaming, as well as an ability to read across disparate PACS without importing data. The unified viewer serves as a "multiology" viewer, for example.

In certain examples, a native reading worklist is provided via the unified viewer. The worklist is intuitive and user defined and can include multi-identifier, multi-document, and multi-institution, for example.

Certain examples provide workflow integration via the unified viewer. Workflow integration includes integration with reporting systems, worklists, voice recognition (VR), electronic medical records (EMR); exporting of measurements; exporting of exam notes; thin slice management; etc.

In certain examples, a workflow manager (WFM) operates in the background to improve performance in retrieving medical images from remote network locations to a client device at which the images are being reviewed. As a result, using the WFM, medical images are directly retrieved from the remote storage without the need to pre-fetch or cache them.

The workflow manager allows a universal viewer to integrate with any remote network storage of medical images, for example.

In certain examples, the WFM allows data, such as digital imaging and communications in medicine (DICOM) format data, including but not limited to images, to be streamed from image storage directly without prefetching or other intermediary action. All data are considered "online" to users, and not archived. The Workflow Manager allows a viewer to quickly retrieve images from remote storage without extra pre-fetching or intermediary action. WFM prioritizes retrieval of metadata and image data based on a fastest route to a user's workstation.

In certain examples, a universal viewer is used for patient diagnosis using images. Remote network storage is used to store the medical diagnostic images. The workflow manager sits between the universal viewer and remote network storage. When images are to be reviewed, the WFM collects metadata about images of the same patient and same study from all available remote network storages simultaneously (or near/substantially simultaneously given memory access, processor, and/or transmission delay) and sends such metadata to the universal viewer. The metadata is called a study file. The purpose of the study file is to enable the universal viewer to receive medical images directly from the closest remote network storage (e.g., regardless of storage vendor). Direct retrieval of medical images from closest storage reduces or minimizes the time to retrieve medical images, allowing doctors to spend more quality time diagnosing images, for example.

To generate the study file, the WFM extracts metadata about one or more image studies from available databases and prioritizes retrieval of medical images from multiple storages. For example, the WFM uses one or more of the following interfaces to achieve this: a database (DB) interface, a DICOM interface, a health level-7 (HL7) interface, etc. The WFM extracts image metadata from multiple products including but not limited to the following products: a PACS, a Web-based or internet-accessible PACS, an enterprise archive (EA), a volume viewer, etc.

The WFM determines where the medical images are stored and employs an algorithm to decide which storage is the fastest from which to retrieve the medical images. In order to make this decision, the WFM maintains a prioritized list of storages against which the WFM automatically checks the image metadata. For example, if the WFM determines that images reside on both a GE Centricity® PACS and an EA, the WFM decides that it is better to stream images from the PACS. Conversely, if the images reside only on the EA, images are directly streamed from the EA, for example.

In certain examples, the prioritization algorithm of the WFM is used when retrieving not only medical images but also when retrieving medical non-image artifacts, including but not limited to structured reports, presentation states, key image notes, etc.

Certain examples provide a highly scalable system because one deployment can have multiple instances of WFMs, multiple image streaming engines, multiple data storages, etc. The scalability of the system allows a number of users to have access to images regardless of storage. In order to provide balanced, controlled access to images, the system groups permutations of a WFM, an image streaming engine, and a storage into a triplet (each triplet includes one WFM, one streaming engine, and one storage). For example, if a deployment has 1 WFM, 1 streaming engine, and 1 Storage, the system has 1 triplet. If a deployment has 2 WFMs, 2 streaming engines, and 2 storages, the system has 2×2×2=8 triplets.

In certain examples, the system interprets each triplet as follows. If a viewer connects to a WFM from a specific triplet and the image lies on the storage from the same triplet, then the viewer uses the image streaming engine from the same triplet to stream the image. This interpretation is applied by the system on a per image basis. If the images of a study reside on different storages, each image of the study is streamed using a relevant triplet. In certain examples, each WFM, image streaming engine, and data storage are combined into triplets according to improved or optimal path over a network.

In certain examples, if an image is stored in two or more storages, the system determines a fastest available storage from which to stream the image (e.g., a scenario with backed-up images). In these examples, each WFM, keeps a prioritized list of storages (e.g., the list can be generated automatically and/or configured by a system administrator). The system interprets the list as follows. If an image is stored on more than one data storage, the WFM chooses the storage with the highest priority on that WFM's list. However, if the WFM does not have a list, the WFM uses a default list to evaluate priority. The location and list analysis can be applied on a per-WFM basis (e.g., a prioritized list of storages is created per WFM), for example.

In certain examples, the per-image and per-WFM determinations can be arranged in the following sequence. First, a viewer connects to a specific WFM to retrieve study/image metadata. Next, the WFM pulls metadata information about an image from one or more available databases. Then, using the metadata information, the WFM creates a list of data stores on which the image resides. The WFM chooses a storage with a highest priority from this list (e.g., from the WFM's custom list, a default system list, a default priority computation, etc.). Using the highest priority storage and a WFM identifier, the WFM chooses a corresponding triplet. Using the selected triplet, the WFM communicates to the viewer the preferred streaming engine from which to stream the image from the selected storage.

FIG. 1 illustrates an example image streaming and workflow management system 100. The system 100 includes a plurality of workflow managers (WFM) 110-111 communicating with a viewer 120 to provide image and associated content. The system 100 also includes a plurality of image streaming engines 130-134 accessing pixel data from a plurality of data storages 140-144. Further, the WFM 110-111 receive a plurality of study metadata from one or more sources 150-153.

As shown in the example of FIG. 1, the viewer 120 requests an image study, and the request is routed to a particular WFM 110-111 to which the viewer 120 is connected. The WFM 110, 111 identifies one or more images in the image study and requests metadata information from one or more available databases 150-153 (e.g., an EA database 150, a PACS integrated medical system (IMS) database 151, a cross-enterprise document sharing for imaging (XDS-i) database 152, a DICOM C-Find query service class provider (SCP) database 153, etc.). Based on the metadata information, the WFM 110-111 determines a location 140-144 for each image in the study (e.g., not necessarily the same location for each image). The WFM 110-111 compares the relevant location(s) 140-144 for a requested image against a priority list (e.g., specific, default, etc.) for the WFM 110-111 to determine a location 140-144 among the eligible location(s) 140-144 from which to retrieve the image. The WFM 110-111 then connects to the streaming engine 130-134 associated with the selected location 140-144 and requests the image from the storage 140-144 via the streaming engine 130-134. The selected image streaming engine 130-134 provides pixel data to the viewer 120, and the WFM 110-111 provides associated metadata. Based on the image pixel data and study metadata, the viewer 120 provides image review and manipulation to a client (not shown), for example.

Thus, certain examples facilitate improved image location and retrieval via a workflow manager for streamlined viewer operation. Certain examples facilitate workflow manager operation in the background while a user interacts with the viewer to retrieve images from one or more remote data stores. Using the workflow manager(s) and streaming engine(s), images can be retrieved directly from remote storage without prefetching or caching images to provide to the viewer. Further, through the configuration and selection of triplets (WFM, streaming engine, and storage), the viewer can integrate with a variety of remote network storage devices/locations for medical images.

Figure 2:
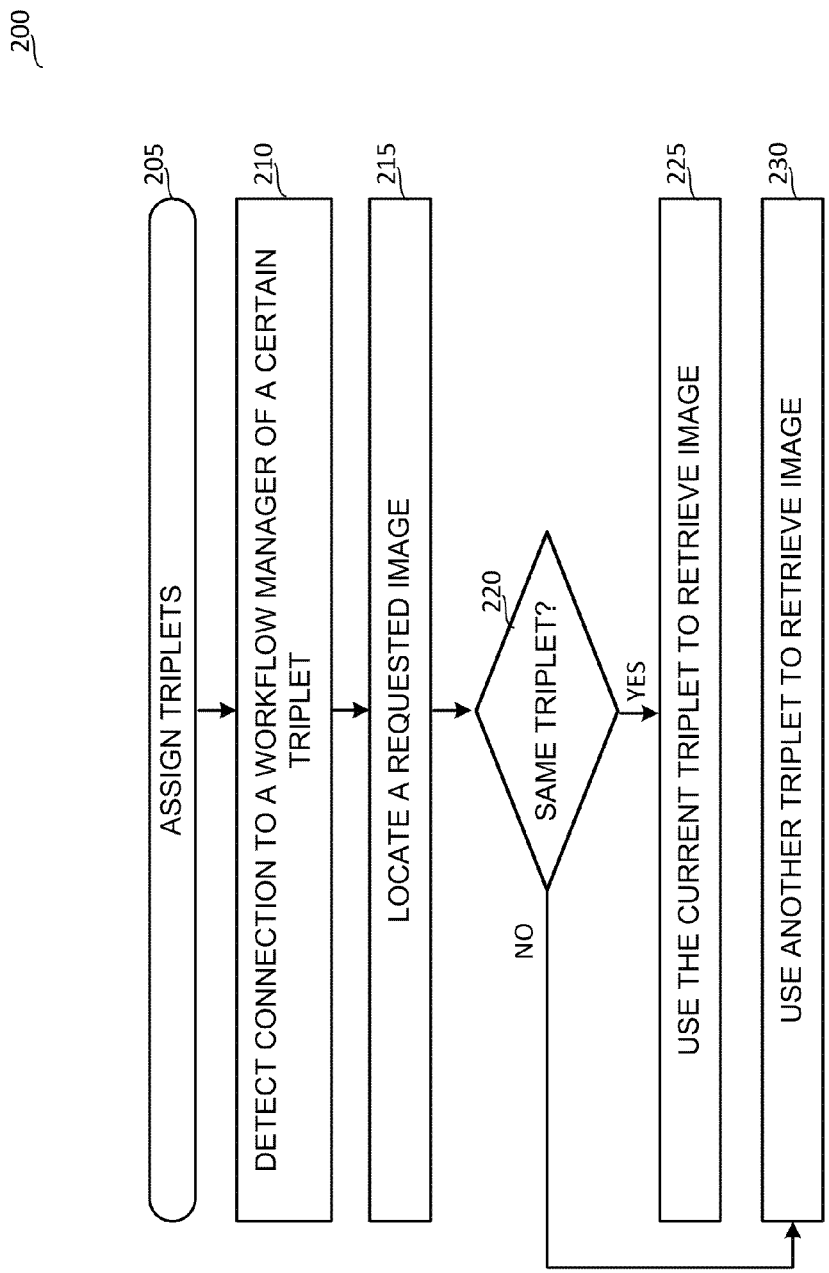
FIG. 2 illustrates a flow diagram of an example method to retrieve image data from one or more storage locations.

FIG. 2 illustrates a flow diagram of an example method 200 to retrieve image data from one or more storage locations. At block 205, one or more triplets are assigned to group a WFM with an image streaming engine and a storage device. For example, if a system has one WFM, one streaming engine, and one storage device, then there is one triplet. If a system has three WFMs, three streaming engines, and three storage devices, then there are three times three times three equals twenty-seven triplets.

At block 210, a connection (e.g., by a viewer) to a particular WFM of a certain triplet is detected. For example, a viewer connects to a WFM from a specific triplet. At block 215, a requested image is located. For example, the viewer requests an image or image study, and the location(s) of the image are determined. At block 220, the location of the image is reviewed to determine whether the image is located in the same triplet as the connected WFM. If yes, at block 225, the current triplet (e.g., the storage device in the selected triplet) is used to retrieve the image. If no, at block 230, another identified triplet is used to retrieve the requested image.

Figure 3:
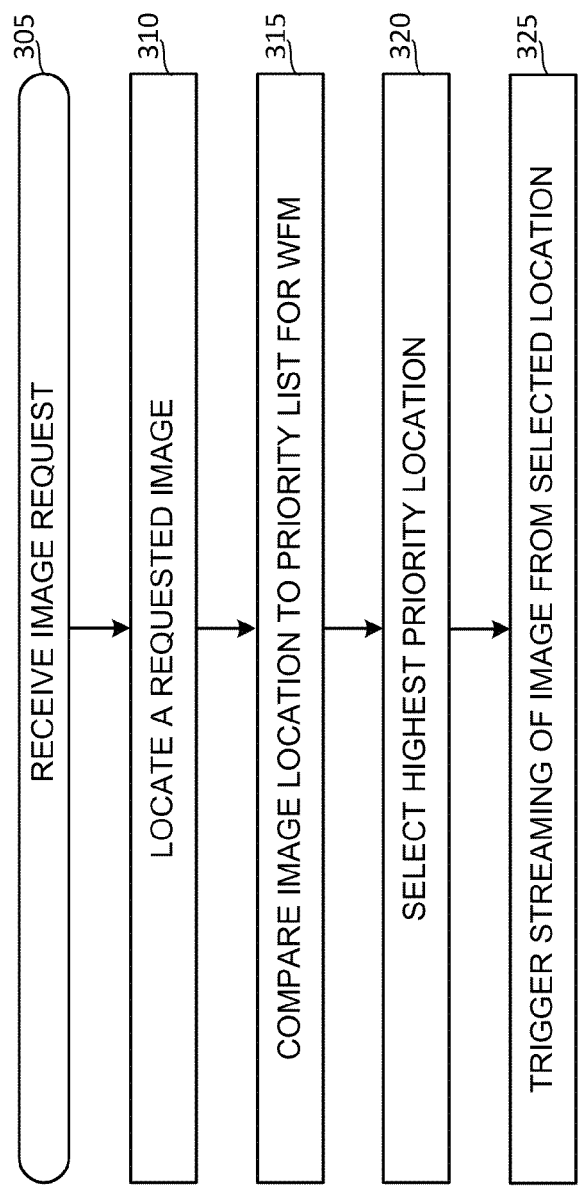
FIG. 3 illustrates a flow diagram of an example method to identify and retrieve image data from a priority storage location.

FIG. 3 illustrates a flow diagram of an example method 300 to identify and retrieve image data from a priority storage location. At block 305, a request for an image is received. For example, a WFM receives an image request from a viewer. At block 310, the requested image is located. For example, the image may be located on one or more storage devices, and a fastest and/or otherwise most convenient storage device is to be identified for image retrieval.

At block 315, identified image location(s) are compared to a prioritized list of storage locations (e.g., custom, default, etc.) maintained with the WFM receiving the image request. At block 320, a highest priority location is identified. For example, if an image lies on more than one storage, then the WFM chooses the storage with the highest priority on the WFM's list. At block 325, the WFM triggers streaming of the image from the selected location.

Figure 4:
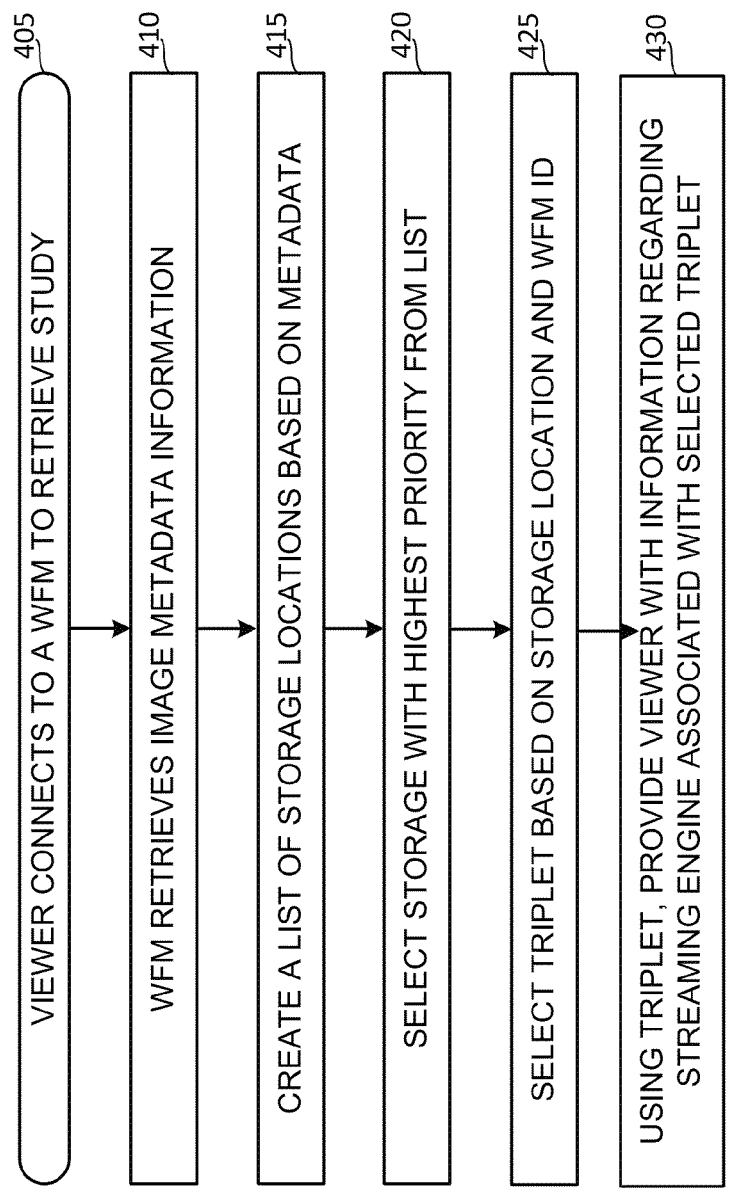
FIG. 4 illustrates a flow diagram of an example method to prioritize image study data retrieval.

FIG. 4 illustrates a flow diagram of an example method 400 to prioritize image study retrieval. At block 405, a viewer connects to a WFM to retrieve an image study and associated metadata. At block 410, the WFM pulls metadata information about a study image from one or more available databases. At block 415, using the retrieved metadata information, the WFM creates a list of storage locations on which the image is stored. In certain examples, rather than a list created by the WFM, a default list is provided.

At block 420, the WFM chooses a storage with highest priority from the list to retrieve the image. At block 425, a triplet of WFM, image streaming engine, and storage device is selected by the WFM based on the selected highest priority storage as well as an associated WFM identifier. At block 430, using the selected triplet, the WFM communicates to the viewer an identity of an associated image streaming engine to stream the image from the selected storage.

Figure 5:
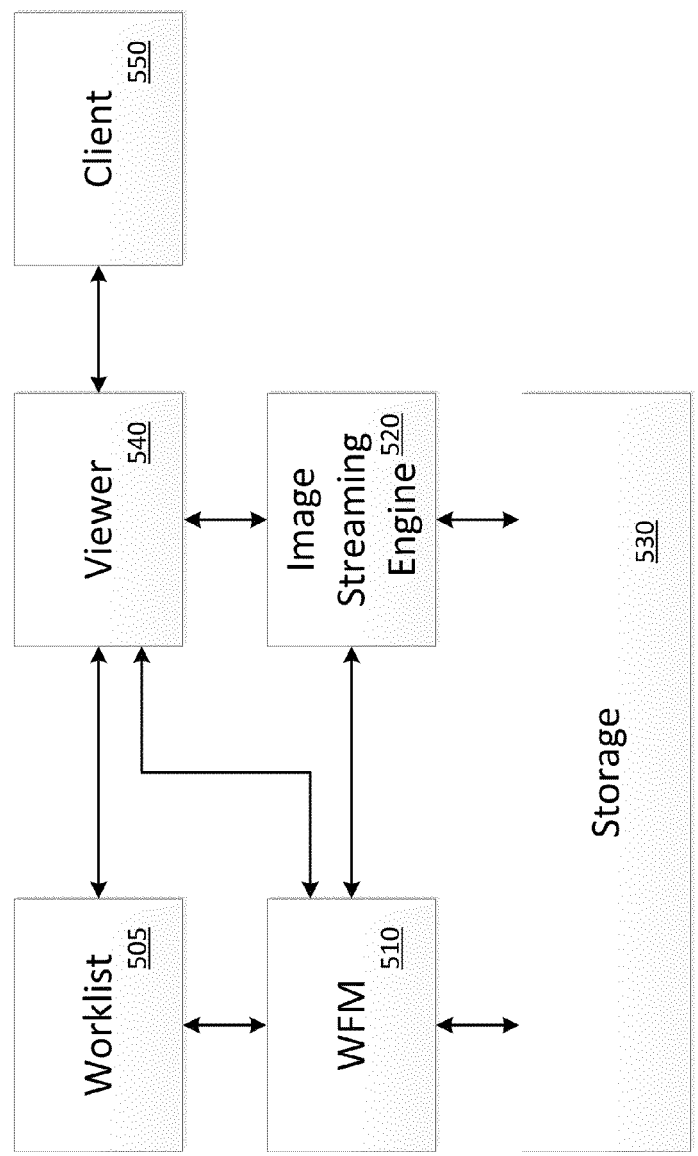
FIG. 5 illustrates an example image review and reporting system including a workflow manager, an image streaming engine, a data storage, and a viewer.

FIG. 5 illustrates an example image review and reporting system 500 including a workflow manager 510, an image streaming engine 520, a data storage 530, and a viewer 540. The viewer 540 communicates with a client browser 550 to send image and associated data for display via the browser 550 and receive input via the browser 550. The workflow manager 510 can operate according to items in a worklist 505, for example.

The WFM 510 identifies a requested image and/or set of images and determines one or more locations at which the request image(s) can be found. This determination can occur on an image-by-image basis, on a study basis, etc., and can be based on or assisted by study metadata information, for example. Image storage locations 530 can be prioritized according to one or more criteria (e.g., speed, proximity, authorization, etc. Based on prioritized location information, the WFM 510 connects the viewer 540 with the image streaming engine 520 to provide image(s) and/or associated information from storage 530 to the viewer 540 and thereby to the client 550.

In certain examples, the viewer 540 is implemented with the system 500 as a zero footprint (ZFP) viewer providing ZFP image viewing and manipulation to the client browser 550 with the assistance of the workflow manager 510 and streaming engine 520. Zero footprint and zero or silent deployment can be facilitated by server-side rendering of images. For example, image processing of advanced applications can occur on the server (e.g., the viewer and/or streaming engine, etc.), rather than the client.

In certain examples, DICOM medical images are streamed directly to a web browser on a client device, without a need for extra or specialized components (e.g., a ZFP browser or viewer). Using WebSockets associated with HTML5 in a browser provides full bi-directional and binary communication without polling or asynchronous JavaScript (Ajax) calls with a Web or other content server. WebSockets (and/or TCP-based sockets) allow a communication channel to be established through which the client and server send messages back and forth to one another at any given time, as long as the communication channel stays active (e.g., the browser page does not change). DICOM medical images can be sent to a user browser without the need for translation (e.g., no base64 encoding or decoding, etc.).

Figure 6:
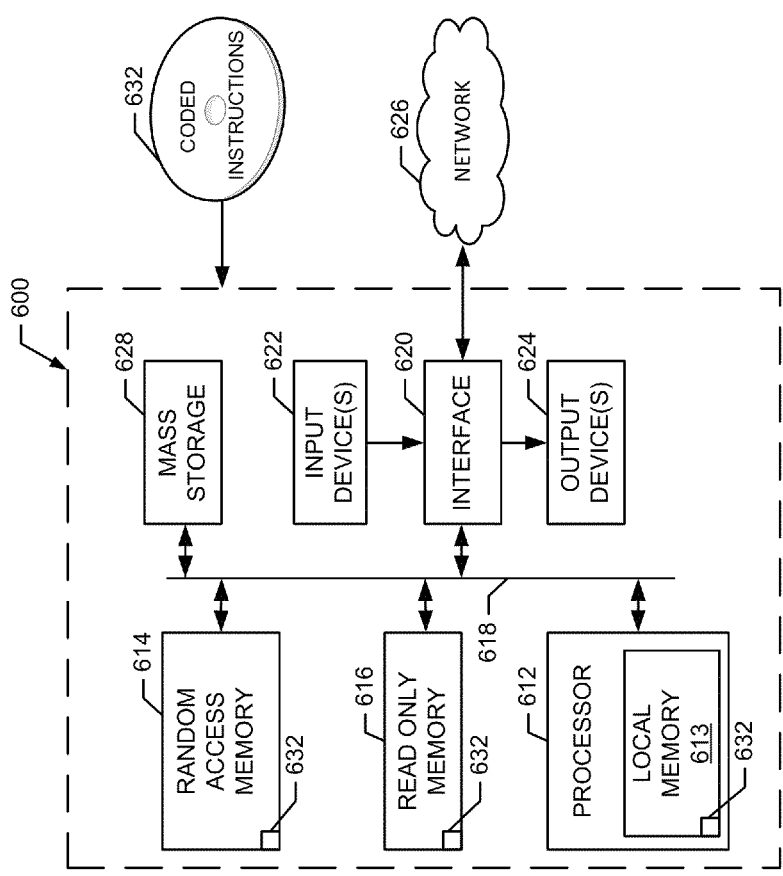
FIG. 6 is a block diagram of an example processor system that may be used to implement systems and methods described herein.

FIG. 6 is a block diagram of an example processor system 610 that may be used to implement systems and methods described herein. As shown in FIG. 6, the processor system 610 includes a processor 612 that is coupled to an interconnection bus 614. The processor 612 may be any suitable processor, processing unit, or microprocessor, for example. Although not shown in FIG. 6, the system 610 may be a multi-processor system and, thus, may include one or more additional processors that are identical or similar to the processor 612 and that are communicatively coupled to the interconnection bus 614.

The processor 612 of FIG. 6 is coupled to a chipset 618, which includes a memory controller 620 and an input/output ("I/O") controller 622. As is well known, a chipset typically provides I/O and memory management functions as well as a plurality of general purpose and/or special purpose registers, timers, etc. that are accessible or used by one or more processors coupled to the chipset 618. The memory controller 620 performs functions that enable the processor 612 (or processors if there are multiple processors) to access a system memory 624 and a mass storage memory 625.

The system memory 624 may include any desired type of volatile and/or non-volatile memory such as, for example, static random access memory (SRAM), dynamic random access memory (DRAM), flash memory, read-only memory (ROM), etc. The mass storage memory 625 may include any desired type of mass storage device including hard disk drives, optical drives, tape storage devices, etc.

The I/O controller 622 performs functions that enable the processor 612 to communicate with peripheral input/output ("I/O") devices 626 and 628 and a network interface 630 via an I/O bus 632. The I/O devices 626 and 628 may be any desired type of I/O device such as, for example, a keyboard, a video display or monitor, a mouse, etc. The network interface 630 may be, for example, an Ethernet device, an asynchronous transfer mode ("ATM") device, an 802.11 device, a DSL modem, a cable modem, a cellular modem, etc. that enables the processor system 610 to communicate with another processor system.

While the memory controller 620 and the I/O controller 622 are depicted in FIG. 6 as separate blocks within the chipset 618, the functions performed by these blocks may be integrated within a single semiconductor circuit or may be implemented using two or more separate integrated circuits.

It should be understood by any experienced in the art that the inventive elements, inventive paradigms and inventive methods are represented by certain exemplary embodiments only. However, the actual scope of the invention and its inventive elements extends far beyond selected embodiments and should be considered separately in the context of wide arena of the development, engineering, vending, service and support of the wide variety of information and computerized systems with special accent to sophisticated systems of high load and/or high throughput and/or high performance and/or distributed and/or federated and/or multi-specialty nature.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method comprising: receiving, at a workflow manager, a request for at least one image and at least one non-image document; identifying, via the workflow manager, a storage location for the requested said at least one image based at least in part on associated metadata information; identifying via the workflow manager, a storage location for the requested said at least one non-image document; selecting, via the workflow manager based on a location priority, an image streaming engine associated with the storage location to stream the requested said at least one image from the storage location to a viewer; selecting, via the workflow manager based on a location priority, said at least one non-image document associated with the storage location to retrieve the requested said at least one image from the storage location to a viewer; triggering, via the workflow manager, streaming of the requested said at least one image from the storage location to the viewer; and retrieving, via the workflow manager, the said at least one non-image document.

2. The method of claim 1, wherein the workflow manager is to be organized in a triplet with an image streaming engine and a storage location, the image streaming engine and the storage location in the workflow manager's triplet to have highest priority on a list of location priority for the requested image.

3. The method of claim 2, wherein the selecting comprises selecting a triplet based on priority of storage location and a workflow manager identifier, and wherein the triggering comprises providing the viewer with information regarding the image streaming engine in the selected triplet with the priority storage location for the requested image.

4. The method of claim 2, wherein the workflow manager is to be provided with a default priority list of storage locations.

5. The method of claim 1, further comprising generating a priority list of storage locations to be compared to one or more locations having the requested image, the storage location to be selected from the priority list based on location priority.

6. The method of claim 1, wherein the triggering comprises triggering, via the workflow manager, streaming of the requested image by providing an identity of the associated image streaming engine to the viewer.

7. The method of claim 1, wherein the workflow manager is to be organized in a triplet with an image streaming engine and a storage location, the image streaming engine and the storage location in the workflow manager's triplet to have highest priority on a list of location priority for the requested said at least one non-image document.

8. The method of claim 2, wherein the selecting comprises selecting a triplet based on priority of storage location and a workflow manager identifier, and wherein the triggering comprises providing the viewer with information regarding the image streaming engine in the selected triplet with the priority storage location for the requested said at least one non-image document.

9. The method of claim 1, further comprising generating a priority list of storage locations to be compared to one or more locations having the requested said at least one non-image document, the storage location to be selected from the priority list based on location priority.

10. The method of claim 1, wherein the triggering comprises triggering, via the workflow manager, streaming of the requested said at least one non-image document image by providing an identity of the associated image streaming engine to the viewer.

* * * * *